US012775114B2

(12) United States Patent
Wang et al.

(10) Patent No.: US 12,775,114 B2
(45) Date of Patent: Oct. 27, 2026

(54) CEMENT BOND EVALUATION IN A WELLBORE

(71) Applicant: Halliburton Energy Services, Inc., Houston, TX (US)

(72) Inventors: Ruijia Wang, Singapore (SG); Yao Ge, Singapore (SG); Xiang Wu, Singapore (SG); Chung Chang, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 446 days.

(21) Appl. No.: 17/943,918

(22) Filed: Sep. 13, 2022

(65) Prior Publication Data

US 2024/0085582 A1 Mar. 14, 2024

(51) Int. Cl.

| | |
|---|---|
| ***G01V 1/50*** | (2006.01) |
| ***E21B 47/005*** | (2012.01) |
| ***G01B 17/06*** | (2006.01) |
| ***G01N 33/38*** | (2006.01) |
| *E21B 47/00* | (2012.01) |
| *E21B 47/14* | (2006.01) |
| *G01V 1/44* | (2006.01) |
| *G01V 1/46* | (2006.01) |
| *G01V 1/48* | (2006.01) |

(52) U.S. Cl.

CPC .............. *G01V 1/50* (2013.01); *E21B 47/005* (2020.05); *G01B 17/06* (2013.01); *G01N 33/383* (2013.01); *E21B 47/00* (2013.01); *E21B 47/14* (2013.01); *G01N 33/38* (2013.01); *G01V 1/44* (2013.01); *G01V 1/46* (2013.01); *G01V 1/48* (2013.01); *G01V 2210/1299* (2013.01); *G01V 2210/1429* (2013.01); *G01V 2210/60* (2013.01)

(58) Field of Classification Search
None
See application file for complete search history.

(56) References Cited

U.S. PATENT DOCUMENTS 3,369,626 A * 2/1968 Zemanek, Jr. ...... E21B 47/0025 367/68
3,371,313 A * 2/1968 Zemanek, Jr. ........... G01V 1/48 367/33
11,681,065 B2 * 6/2023 Hornby .................. G01V 20/00 702/11

(Continued)

FOREIGN PATENT DOCUMENTS

| | | | | |
|---|---|---|---|---|
| CA | 2747275 C | * | 3/2015 | ............... G01V 1/52 |
| GB | 2494780 A | * | 3/2013 | ........... E21B 29/005 |
| WO | WO-2017172805 A1 | * | 10/2017 | ............ E21B 47/14 |

OTHER PUBLICATIONS

"PCT Application No. PCT/US2022/076446, International Search Report and Written Opinion", May 26, 2023, 11 pages.

(Continued)

*Primary Examiner* — Arleen M Vazquez
*Assistant Examiner* — Leonard S Liang
(74) *Attorney, Agent, or Firm* — DeLizio, Peacock, Lewin and Guerra, LLP

(57) ABSTRACT

Cement bonding evaluation and logging in a wellbore environment are described. The cement bonding evaluation is performed using data associated with and processed from the measurement of sonic waves directed to and dissipated by the casing present in the wellbore.

20 Claims, 9 Drawing Sheets

(56) References Cited

U.S. PATENT DOCUMENTS

| | | | | |
|---|---|---|---|---|
| 2007/0140055 | A1* | 6/2007 | Tello | G01V 1/44 367/25 |
| 2011/0280101 | A1* | 11/2011 | Wang | G01V 1/46 367/25 |
| 2011/0280102 | A1* | 11/2011 | Wang | G01V 1/50 367/31 |
| 2011/0286307 | A1* | 11/2011 | Wang | E21B 17/1078 367/82 |
| 2012/0330554 | A1 | 12/2012 | Ross et al. | |
| 2015/0198732 | A1* | 7/2015 | Zeroug | E21B 47/005 367/35 |
| 2015/0219780 | A1* | 8/2015 | Zeroug | E21B 49/003 702/6 |
| 2015/0322782 | A1* | 11/2015 | Khajeh | E21B 49/08 175/48 |
| 2015/0331134 | A1 | 11/2015 | Haldorsen et al. | |
| 2016/0146762 | A1* | 5/2016 | Huang | G01N 29/069 73/598 |
| 2016/0195634 | A1* | 7/2016 | Frey | G01V 3/30 324/338 |
| 2016/0209540 | A1* | 7/2016 | Frey | G01V 3/28 |
| 2017/0350231 | A1* | 12/2017 | Merciu | G01V 1/50 |
| 2018/0045844 | A1* | 2/2018 | Oshima | G01V 1/44 |
| 2018/0149019 | A1* | 5/2018 | Bose | E21B 47/005 |
| 2019/0055830 | A1 | 2/2019 | Skataric et al. | |
| 2019/0145241 | A1* | 5/2019 | Yao | E21B 47/002 348/85 |
| 2019/0179048 | A1* | 6/2019 | Syresin | G01V 1/46 |
| 2019/0376380 | A1 | 12/2019 | Zhang et al. | |
| 2020/0072040 | A1 | 3/2020 | Liu et al. | |
| 2021/0123339 | A1* | 4/2021 | Steel | E21B 33/134 |
| 2021/0246777 | A1* | 8/2021 | Zhao | E21B 47/005 |
| 2022/0333477 | A1* | 10/2022 | Kalyanraman | E21B 47/005 |
| 2022/0390637 | A1* | 12/2022 | Yogeswaren | G01V 1/46 |
| 2023/0194743 | A1* | 6/2023 | Wang | E21B 47/0025 166/253.1 |
| 2023/0220764 | A1* | 7/2023 | Zhao | E21B 47/005 367/35 |
| 2023/0417942 | A1* | 12/2023 | Steel | G01V 1/50 |
| 2024/0085583 | A1* | 3/2024 | Garcia Roman | G01V 1/50 |

OTHER PUBLICATIONS

Wang, et al., "The Wavefield of Acoustic Logging in a Cased-hole With a Single Casing—Part I: a Monopole Tool", Geophysical Journal International, vol. 212, Oct. 12, 2017, 15 pages.

* cited by examiner

CEMENT BOND EVALUATION IN A WELLBORE

TECHNICAL FILED

This disclosure generally relates to production logging of a cased wellbore extending into a subterranean formation, and more specifically to cement evaluation of the cased wellbore.

BACKGROUND

Operations involving production logging of a cased wellbore that extends into a subterranean formation may include cement monitoring and/or evaluation of the cement in spaces surrounding the outer surface of the casing. These evaluations may be important because when pressure imbalances cause crossflows through poorly cemented sections, excessive production of unwanted fluids might occur. Further, a section or large portions of the wellbore to be evaluated may include a production tubing extending within and through the interior annulus encircle by the casing, and wherein the production logging is to be performed with the production tubing remaining in place. As such, there is a high demand for a solution of cement bond logging and evaluation that can be performed for example through production tubing in order to save time and money.

Figure 1:
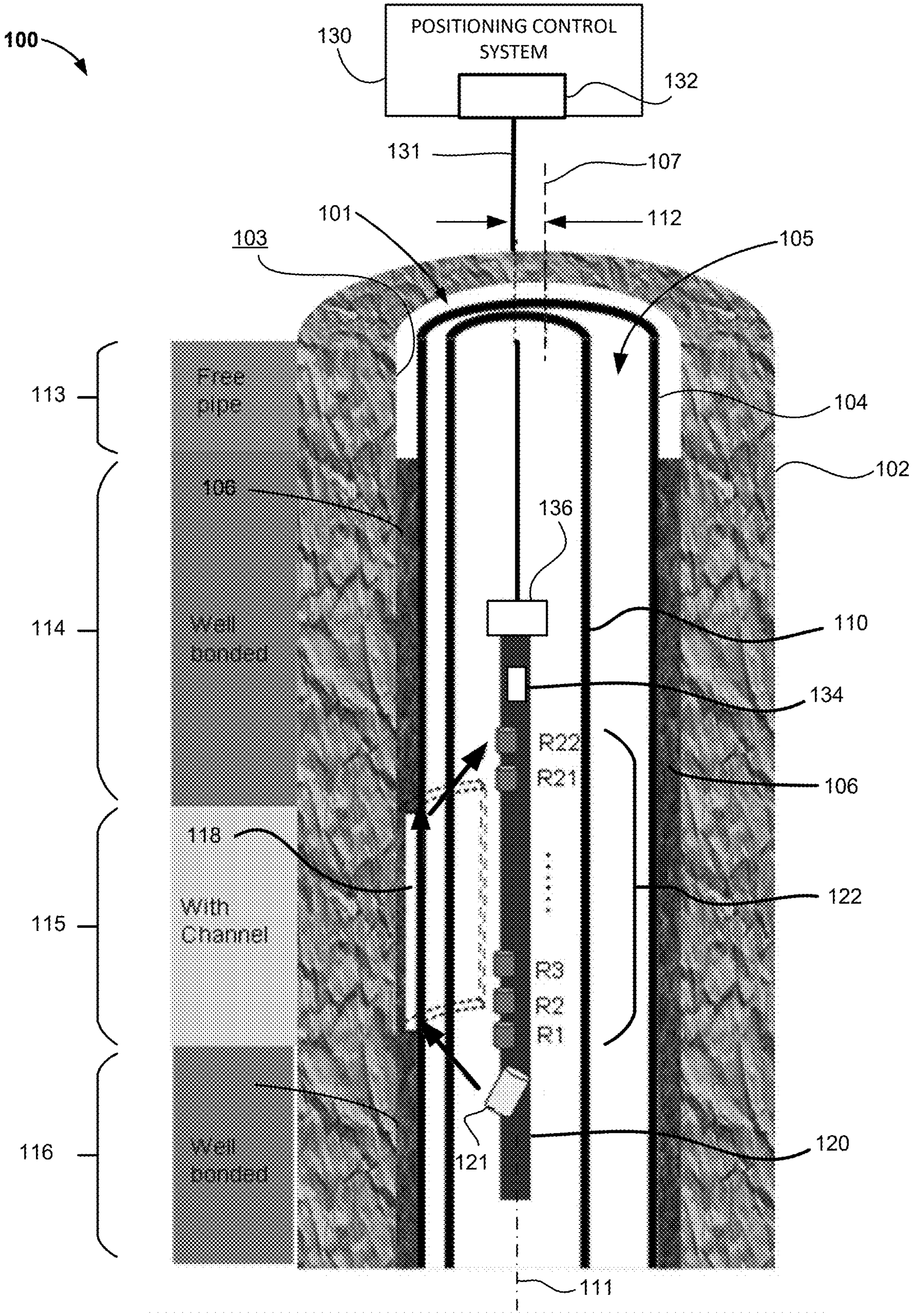
FIG. 1 illustrates a perspective view of a system comprising a sonic tool positioned in a casing of a wellbore, according to various embodiments.

The drawings are provided for the purpose of illustrating example embodiments. The scope of the claims and of the disclosure are not necessarily limited to the systems, apparatus, methods, or techniques, or any arrangements thereof, as illustrated in these figures. In the drawings and description that follow, like parts are typically marked throughout the specification and drawings with the same or coordinated reference numerals. The drawing figures are not necessarily to scale. Certain features of the invention may be shown exaggerated in scale or in somewhat schematic form, and some details of conventional elements may not be shown in the interest of clarity and conciseness.

DETAILED DESCRIPTION

In the following detailed description of the illustrative embodiments, reference is made to the accompanying drawings that form a part hereof. These embodiments are described in sufficient detail to enable those skilled in the art to practice the techniques and methods described herein, and it is understood that other embodiments may be utilized and that logical structural, mechanical, electrical, and chemical changes may be made without departing from the scope of the disclosure. To avoid detail not necessary to enable those skilled in the art to practice the embodiments described herein, the description may omit certain information known to those skilled in the art. The following detailed description is, therefore, not to be taken in a limiting sense.

In various embodiments, production logging of a wellbore system requires cement monitoring, which in various instances requires the logging of a wellbore including the existence of a tubing, such as a production tubing, present in the portion of the wellbore to be logged. When pressure imbalance causes crossflow through poorly cemented sections of the casing, excessive production of unwanted fluids might occur. There is a high demand for a solution of cement bond logging, including wellbore with tubing, to save time and money. Not only in the area of production logging, the operation of well abandonment is also eager for the technique of cement bond logging through tubing. A wellbore or well system that comes close to the end of its operating life cycle must be plugged and abandoned (P&A). One possible way to cut the costs during P&A operations is to leave most of the production tubing in wells so that the rig time and money could be significantly reduced. As an essential preparation task for P&A operations, well integrity such as cement bond condition behind casing must be tested beforehand.

Previous efforts of through tubing cement evaluation include using the frequency spectrum of recorded signals, MIE resonance, and general borehole sonic dispersion response. These methods provide a free-pipe indicator used to reflect the position of free-pipe zones or the top of the cement. However, limited to the omnidirectional monopole transmitter they use, these methods have limited capability in detecting and locating azimuthal bonding information behind casing.

This disclosure describes methods and techniques that utilize the directional source and receivers with rotation capability to scan the casing A0 waves for evaluating the materials behind the casing of a wellbore. Spatial filters in the slowness-frequency domain are used to extract the casing-related A0 waves. Amplitude or attenuation information of casing A0 waves is used to reveal bonding conditions behind the casing.

Cement evaluation (TTCE) is challenging through tubing as most sonic signals are limited in the steel tubing. Traditional methods using 20 kHz acoustic signals or ultrasonic signals encounter issues for TTCE. The systems, apparatus, method and techniques as described here utilize low-frequency casing pseudo A0 waves having a short wavelength with local-focused energy to generate information related to the quality of cement bonding outside a casing and within a wellbore structure. The amplitude information from the A0 waves dispersed by the casing reflects zones with channels behind the casing and within the cement. Additionally, in various embodiments, to enable azimuthal detection A0 waves are excited and captured by unipole transmitters and unipole receivers, which are mounted at a rotary head of a sonic tool deployed with the casing of the wellbore. The casing A0 signals at any azimuths are measured by rotating a transmitter and one or more receivers located on the sonic tool. The bonding condition behind the casing can be further extracted from the amplitude of measured casing A0 waves received at the one or more receivers of the sonic tool.

Various aspects and features of the methods and techniques described herein include:

- Exciting low-frequency signals which can go through the casing and form casing A0 waves;
- The way of exciting low-frequency A0 waves by unipole sources and receivers mounted at a rotary head;
- The workflow to extract A0 amplitude map in the slowness-frequency domain;
- The workflow to extract A0 amplitude map in the time-spatial domain; and
- A0 map eccentricity calibration.

The methods and techniques as described herein are applicable for the evaluation of cement bonding to a casing in systems with and without a production tubing being present within the casing. The technique enables the through tubing cement evaluation with low-frequency casing A0 waves. Lamb waves exhibit velocity dispersion; their propagation velocity depends on the frequency (or wavelength) and the elastic constants and density of the material. This phenomenon is central to the study and understanding of wave behavior in plates or a pipe. For the lamb wave propagating in a cylindrical pipe, the dispersions of the lamb waves rely on the pipe's thickness and diameter.

The symmetrical and antisymmetric zero-order modes deserve special attention. These modes have "nascent frequencies" of zero. Thus they are the only modes that exist over the entire frequency spectrum from zero to indefinitely high frequencies. In the low-frequency range (i.e., when the wavelength is greater than the pipe thickness) these modes are often called the "extensional mode" and the "flexural mode" respectively, terms that describe the nature of the motion and the elastic stiffnesses that govern the velocities of propagation. The elliptical particle motion is mainly in the plane of the pipe for the symmetrical, extensional mode and perpendicular to the plane of the pipe for the antisymmetric, flexural mode. These characteristics change at higher frequencies. These two modes are the most important and often used in cement bond logging because (a) they exist at all frequencies and (b) in most practical situations, they carry more energy than the higher-order modes. The zero-order symmetrical mode (designated S0) and the zero-order antisymmetric mode (designated A0) in a casing or tubing pipe are slightly different from these waves in a plate.

FIG. 1 illustrates a perspective view of a system 100 comprising a sonic tool positioned in a casing of a wellbore, according to various embodiments. As shown in FIG. 1, a borehole 101 extends for some depth through a formation material 102. Formation material 102 may be any material extending below the Earth's surface. In various embodiments, formation material 102 extends through terrestrial material, but in various embodiments formation material 102 may be formed at or below the bottom of a body of water, such a lake, a sea or an ocean bed. As shown in FIG. 1, system 100 includes a casing 104, which may comprise metal pipes, and which extends along a longitudinal center axis 107 of the borehole. Casing 104 encircles the longitudinal center axis 107 of the borehole 101, forming an annulus 105 within the casing. Proportions of the space between the casing and an inner surface 103 of the borehole may be filled with cement 106.

In various embodiments, not all portions of the space between the casing 104 and the inner surface 103 of the borehole 101 are filled with cement. As illustrated in FIG. 1, the portion of the casing 104 extending over the depth range of the borehole 101 indicated as "Free Pipe" to the left of bracket 113 does not include cement 106 in the space between the casing and the inner surface 103 of the borehole. In addition, the portions of the casing 104 extending over the depth ranges of the borehole 101 indicated as "Well Bonded" to the left of brackets 114 and 116, respectively, include cement 106 in the space between the casing and the inner surface 103 of the borehole. Further, portions of the casing extending over the depth ranges of borehole 101 may include some portions of the space between the casing 104 and the inner surface 103 filled with cement 106, but may include voids or spaces, referred to as a "channel," where the cement is missing and/or has separated from and/or is not well bonded to the casing. An example of a portion of the casing 104 included in system 100 where a channel 118 is present in the cement located in the space between the casing 104 and the inner surface 103 of the well bore is illustrated in FIG. 1 as the area to the right of bracket 115, the area designated as "With Channel" in the figure.

A sonic tool 120 is configured to be placed within the casing 104, and using the devices, methods, and techniques as described herein, gather measurements and process these measurements to produce data that may be used to evaluate the bonding and fill of the cement, and/or the absence of cement, within various portions of the space between the casing and the inner surface of the borehole. As shown in FIG. 1, sonic tool 120 is deployed within the casing 104 so as to be suspended at some depth within the borehole 101. Sonic tool 120 may be suspended by a cable 131 from a positioning control system 130. In various embodiments, positioning control system 130 includes various devices, such as a cable spool or winch device, configured to allow for controlled release and retraction of cable 131 within the casing 104, thus controlling the relative depth-wise positioning of the sonic tool 120 at a desired depth or range of depths within the casing 104. As shown in FIG. 1, sonic tool 120 is further positioned with a tubing 110. Tubing 110 in various embodiments is a production tube, which may exist in the well in order to bring materials, such as gas or oil, from various depths with the borehole to a surface of the borehole for further processing. However, inclusion of tubing 110 is not necessary for the operation of system 100 and sonic tool, 120, and in various embodiments sonic tool 120 may be deployed within casing 104 without the presence of tubing 110.

Sonic tool 120 includes at least one transmitter 121. Transmitter 121 is positioned on sonic tool 120, for example on an outer surface of the tool body of the sonic tool, and is configured to transmit sonic signals from the transmitter that are directed toward the casing 104 in the area adjacent to the location of the transmitter within the casing. Sound waves that propagated through the casing 104, along with propagating through any fluid within the casing (and/or the tubing 110 when the tubing is present), are received at one or more receivers located on the sonic tool 120. The number of receivers included on a given embodiment of sonic tool 120 is not limited to a particular number of receivers, and may be a positive integer number of receivers, including in various embodiments a single (one) receiver. As shown in FIG. 1, an embodiments of sonic tool 120 may include twenty-two receivers, as designated in FIG. 1 as R1-R22 and by bracket 122. The sound waves as received by the one or more receivers of the sonic tool 120 may be processed using signal processing, for example analog-to-digital (A/D) signal processing, filtered to remove undesired noise or sound waves in undesired frequency ranges, and/or other signal processing procedures. Following any signal processing that is to be performed on the received sonic signals, the information present in the received sound signals may be processed using some or a combination of the methods and techniques as described in this discourse in order to generate data that can be used to evaluate the cement bonding qualities of the cement present, or lack of cement present, in the areas of the casing and borehole where the sonic signals were transmitted and received by the sonic tool 120.

In various embodiments, some or all of the signal processing and/or data generation associated with the transmission and receiving of sound signal performed by the sonic tool may be performed by one or more processors included in a computing section 134 of the sonic tool. Computing section 134 may include computer or microprocessors and associated devices, such as computer memory and network interfaces, which allow the computing section 134 to perform any of the signal processing operations and/or data analysis processes as described in this disclosure in order to generate data for cement bonding evaluation. In various embodiments, computing section 134 includes memory devices where data associated with the operation of the sonic tool 120 and/or data generated as a result of the operation of the sonic tool may be stored, and which can be retrieved from these memory devices at a later time when the sonic tools is removed from the borehole where it was deployed and operated. In various embodiments, computing section 134 includes a network interface configured to allow sonic tool 120 to transmit data, such as raw signal data from waveforms captured by the receiver of the sonic tool, processed signals generated by the processing the captured waveforms, and/or other data generated from the captured waveforms, to another device, such as positioning control system 130, for example in real-time. Transmission of the data to or from sonic tool 120 to another device such as positioning control system 130 may utilize a transmission line incorporated into cable 131 to carry the data between the devices. In various embodiments, transmission to and/or from sonic tool 120 to another device such as positioning control system 130 may be performed using a wireless transmission.

System 100 may include various devices configured with regards to the positioning of sonic tool 120 within the casing 104 (and within tubing 110 when present). In various embodiments, positioning control system 130 includes an actuator 132 that is configured to control the depth-wise positioning of the sonic tool 120 within the casing 104 by controllably releasing and retracting, at different times, the length of cable 131 extended into the borehole 101. In various embodiments, positioning control system 130 determines at what depth to position and reposition the sonic tool 120 based on information transmitted to the position control system from the sonic tool, for example as provided by the computing section 134 of the sonic tool. With regards to the rotational positioning of the sonic tool 120, in various embodiments actuator 132 controls the rotational positioning, and thus the azimuthal orientation of the sonic tool, by rotational forces applied to the sonic tool through cable 131. In various embodiment, positioning control system 130 determines the rotational positioning and repositioning of the sonic tool 120 based on information transmitted to the position control system from the sonic tool, for example as provided by the computing section 134 of the sonic tool. In various embodiments, sonic tool 120 includes a local rotational actuator, such as rotational actuator 136, which may be coupled to the sonic tool and to cable 131, and is configured to provide rotational motion and control of the rotational position of the sonic tool within the casing 104 (and within tubing 110 when present).

A "unipole transmitter" or a "unipole receiver" when utilized as part of a sonic tool, such as sonic tool 120, refers to a sonic transducer that can emit/receive signals to/from a specific direction. The transducer's transmitting or receiving pattern depends on the transducer itself and its packaging. For example, FIG. 1 refers to transducers that are installed on one side of the tool body. The tool body of the sonic tool blocks most of the signals that go through it; thus, the primary energy of the transducer goes to the front of the transducer. Such transducers are unipole sources or receivers. By rotating the tool body of the sonic tool, these unipole transmitters and unipole receiver(s) may be used to obtain the response signals at different azimuths, include all azimuths around the casing 104 within the borehole. Further, by raising and/or lowering the depth-wise position of the sonic tool, these same unipole transmitters and unipole receiver(s) may be used to obtain response signals over a range of depths with the wellbore.

In operation, the sonic tool is positioned at a desired location with a cased borehole, and operated to generate sonic signals that are transmitted from the transmitter of the sonic tool toward and into the casing. One or more receivers receive the sonic signals propagated through the casing, and the received signals are then processed using the techniques and methods as described herein to provide data that may be used to evaluate the quality of the cement bonding present outside of the casing within the borehole. One or more actuators may be used to reposition the sonic tool, both relative to the depth and rotational position of the sonic tool, in order to gain information about the cement bonding qualities over a range of depths and/or a range of azimuthal orientations.

In addition, embodiments of system 100 are not limited to the acoustic system with a unipole transmitter and unipole receivers. Embodiments as described herein may be applied to combinations of different sources and receivers. For example, monopole sources and unipole receivers, dipole sources and unipole receivers, or unipole sources and monopole receivers may be used in various embodiments.

In various embodiments, the signals received at the receivers of the sonic tool may need to be calibrated or provided with correction due to the fact that the relative position of the sonic tool may not correspond to the center axis of the casing, wherein the sonic tool may be poisoned closer to one side of the casing compared to an opposite side of the casing. As an example, as illustrated in FIG. 1, the sonic tool extends along its longitudinal center axis 111. However, the longitudinal center axis 111 of the sonic tool is not collinear with the longitudinal center axis 107 of casing 104, but instead is offset by an eccentric offset distance 112. This eccentric offset distance 112 may affect the measurements of the received sonic waveforms at different azimuthal orientations of the sonic tool. Embodiments of the methods as further described below include techniques to compensate and/or correct for the effects of this eccentric offset distance when operating the sonic tool with the borehole.

Figure 2:
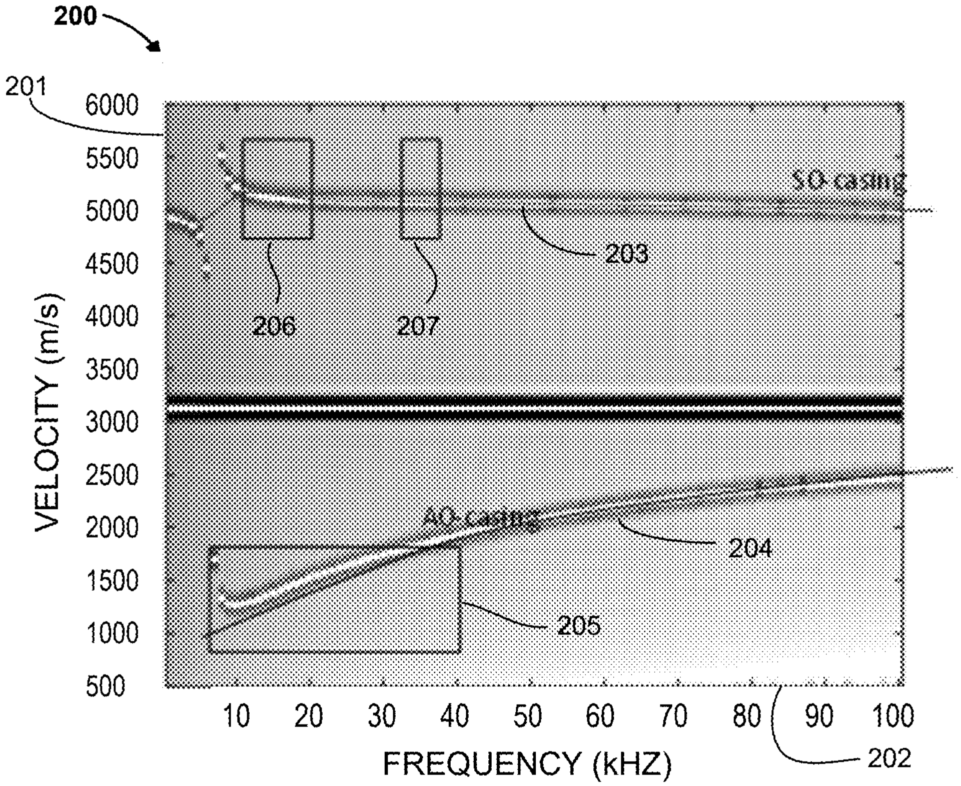
FIG. 2 shows a graph illustrating dispersion of S0 and A0 waves in a free pipe without fluid inside and outside the pipe, according to various embodiments.

FIG. 2 shows a graph 200 illustrating dispersion of S0 and A0 waves in a free pipe without fluid inside or outside of the pipe, according to various embodiments. Graph 200 includes a vertical axis 201 indicative of velocity of the waves in pipe in meters/second (m/s), and a horizontal axis 202 indicative of the frequency of the waves in kilohertz (kHz). Graphical line 203 indicates the velocities over the frequency ranges for S0 waves. Graphical line 204 indicates the velocities over the frequency ranges for A0 waves. Window 205 indicates A0 waves at lower frequencies (approximately 5 kHz to 40 kHz). Window 206 includes S0 waves over a lower frequency range of approximately 10 to 20 kHz, and window 207 includes S0 waves present in the pipe over a higher frequency range of 30 to 38 kHz.

The S0 waves and A0 waves have interfered with each other at low frequencies. The A0 approaches and takes the position of the S0 dispersion at low frequencies, while the high-frequency S0 has a cutoff frequency at the frequency when A0 waves take the place of S0 waves. This phenomenon is due to the curvature of the pipe, and the cutoff frequency is related to the diameter of the pipe. Although modes are coupled, the features of these waves stay the same. For instance, the modes with speeds close to 5000 m/s all show the property of S0 waves; the wave modes with a slowness less than the pipe shear slowness show the property of A0 waves.

Figure 3:
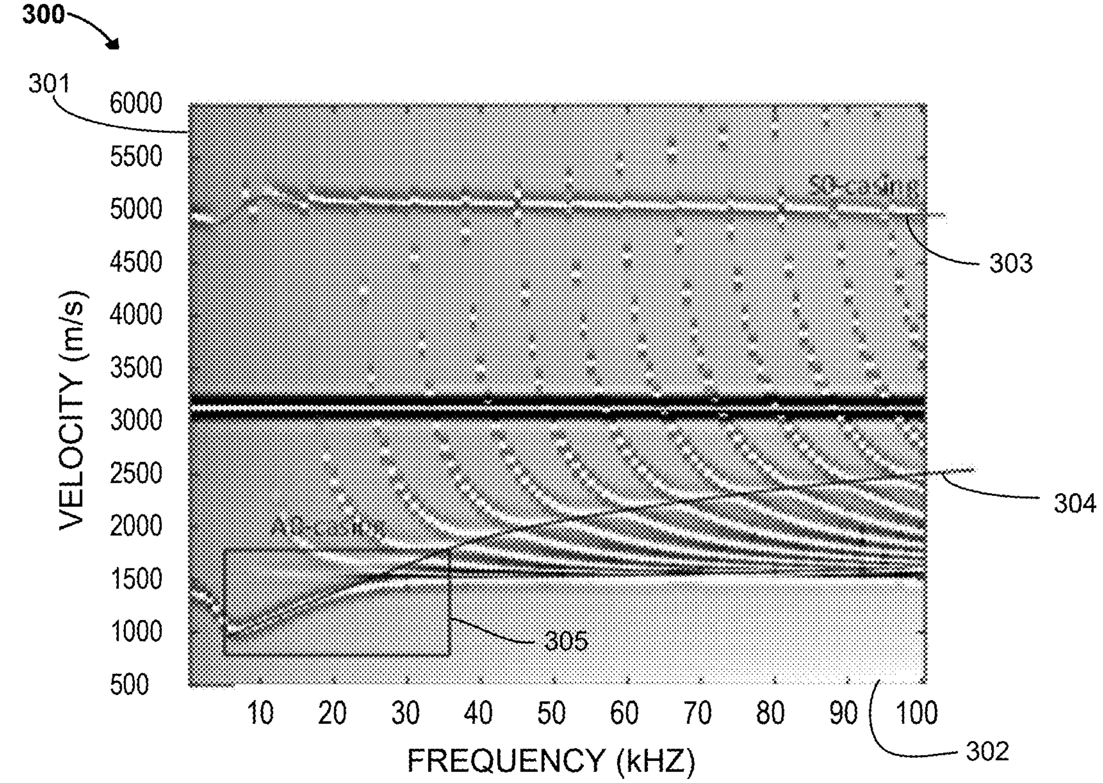
FIG. 3 shows a graph illustrating dispersion of S0 and A0 waves in a fluid filled pipe, according to various embodiments.

FIG. 3 shows a graph 300 illustrating dispersion of S0 and A0 waves in a fluid filled pipe, according to various embodiments. Graph 300 includes a vertical axis 301 indicative of velocity of the waves in the pipe in meters/second (m/s), and a horizontal axis 302 indicative of the frequency of the waves in kilohertz (kHz). Graphical line 303 indicates the velocities over the frequency ranges for S0 waves. Graphical line 304 indicates the velocities over the frequency ranges for A0 waves. Window 305 indicates A0 waves at lower frequencies (approximately 5 kHz to 35 kHz).

The lamb waves in a pipe are different from those in a plate, and therefore are referred to as pseudo-lamb waves. In the frequency range of interest, for example over the range included in window 305, the pseudo-Lamb waves are coupled with the wave motions propagating in the fluid (fluid mode, including Stoneley waves, and high order of fluid modes). For example, the A0 waves approach the Stoneley waves at low frequencies, and are coupled with other fluid modes at high frequencies. Although modes are coupled, the features of these pseudo-lamb waves stay the same. In other words, the wave motions with slowness values close to the original lamb wave slowness (not coupled with the fluid modes, solid lines in FIG. 2), show similar behaviors to the original lamb waves.

It has been demonstrated that the lamb waves are sensitive to the materials surrounding the plate or pipe. When the surrounding materials change, the properties of the lamb waves change. Thus, the lamb waves can be used to understand the material behind the plate or pipe. In various embodiments, the low-frequency casing pseudo A0 waves have a short wavelength with local-focused energy. Its amplitude reflects zones with channels. Additionally, to enable azimuthal detection, A0 waves are excited and captured by unipole transmitters and unipole receivers, which are mounted at a rotary head. The casing A0 signals at any azimuths are measured by rotating the transmitter and receiver(s). The bonding condition behind the casing can be further extracted from the amplitude and attenuation of the measured low-frequency casing A0 waves.

Figure 4:
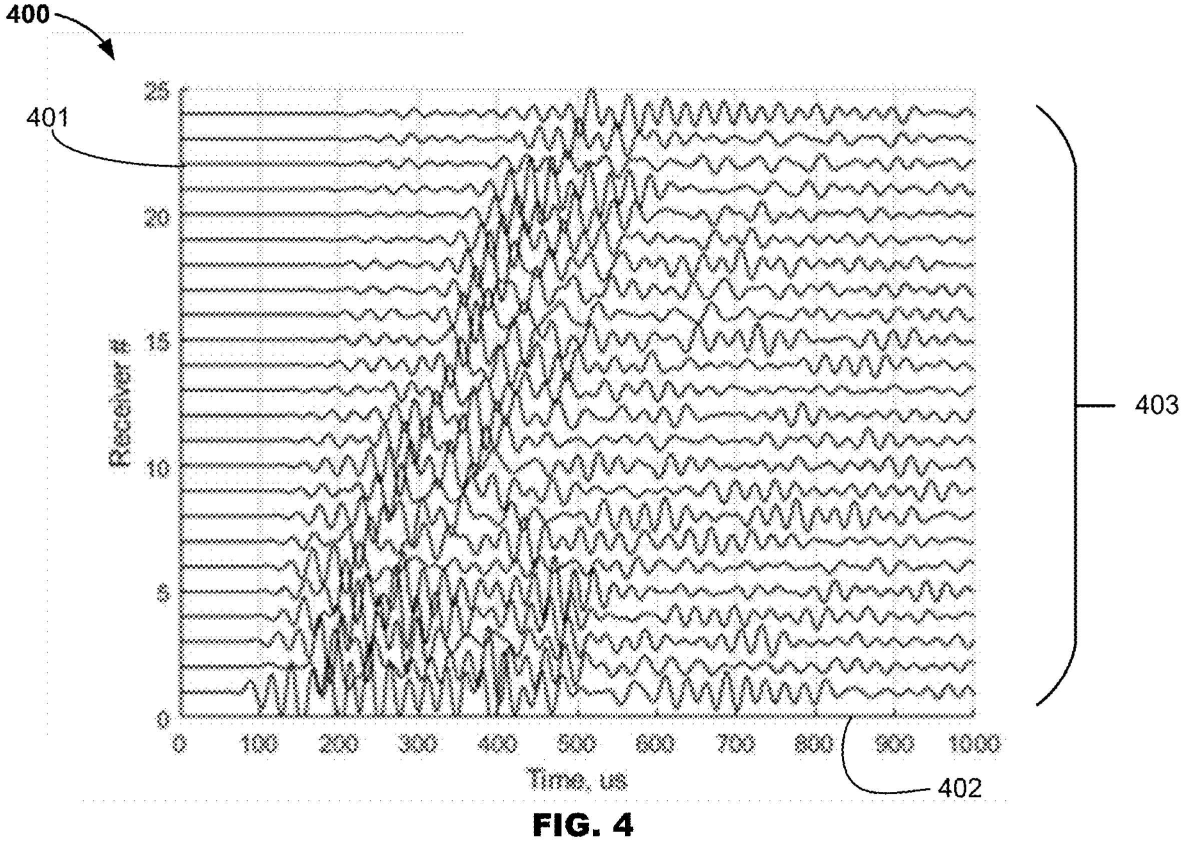
FIG. 4 shows a graph illustrating an example of waveforms measured by a sonic tool comprising a unipole transmitter and a sets of unipole receivers positioned at a fixed depth and a fixed azimuth within a casing of a wellbore, according to various embodiments.

FIG. 4 shows a graph 400 illustrating an example of waveforms measured by a sonic tool comprising a unipole transmitter and a sets of unipole receivers positioned at a fixed depth and a fixed azimuth within a casing of a wellbore, according to various embodiments. Graph 400 includes a vertical axis 401 showing the numbering for the individual receivers included in the sonic tool, and a horizontal axis 402 indicative of time in microseconds (μs). The individual graphical lines, generally indicated by bracket 403, show the respective amplitude responses from each of the receivers 1-24 over time. Embodiments of examples of waveforms may include a different number of receivers generating a corresponding number of waveforms, for example receivers 1-22 as illustrated and described above with respect to system 100 (FIG. 1). In graph 400, the waveform data are in the spatial-temporal domain. Each receiver represents a different spatial position. Each receiver records time series, which carry essential information about the bonding condition behind the casing where the acoustic measurements are being collected by the receivers.

In various embodiments, these waveforms may be processed using the methods and techniques as further described herein to provide information about the quality of cement bonding associated with a wellbore casing, such as casing 104 and cement 106 as illustrated and described with respect to FIG. 1.

In various embodiments, waveforms such as the waveforms shown in graph 400 are input into a workflow involving processes for use in performing cement evaluation based on low-frequency A0 waves. In various embodiments, the waveforms measured by receivers of a sonic tool at the rotary head are inputted into computer application(s) were one or more computer processors, (such as computer processor(s) 1201, FIG. 12), performed the workflow processes on the inputted waveform. In various embodiments, a slowness-frequency semblance analysis, for example, Differential-Phase Frequency-semblance (DPFS), is applied to a set of selected data to extract the dispersion of the target A0 waves.

Based on the extracted dispersion of the target A0 waves, for each depth and azimuth, the raw waveform data are converted to a slowness-frequency amplitude map in the slowness-frequency domain, for example, by the beamforming method or the T-p transform. Then the amplitude of the target A0 wave may be extracted from the slowness-frequency amplitude map using a slowness-frequency window determined by the slowness-frequency semblance analysis. At this step, displaying the amplitude values in the depth-azimuth plane yields the raw amplitude map. Next, with the tubing eccentricity information that are generated from the third interface echo (TIE), an eccentricity calibration processing may be performed to remove the tubing eccentricity effect. A baseline of the well-bond zone response and map the two-dimensional (depth-azimuthal) cement bond image is then identified from the calibrated amplitude image.

Figure 5:
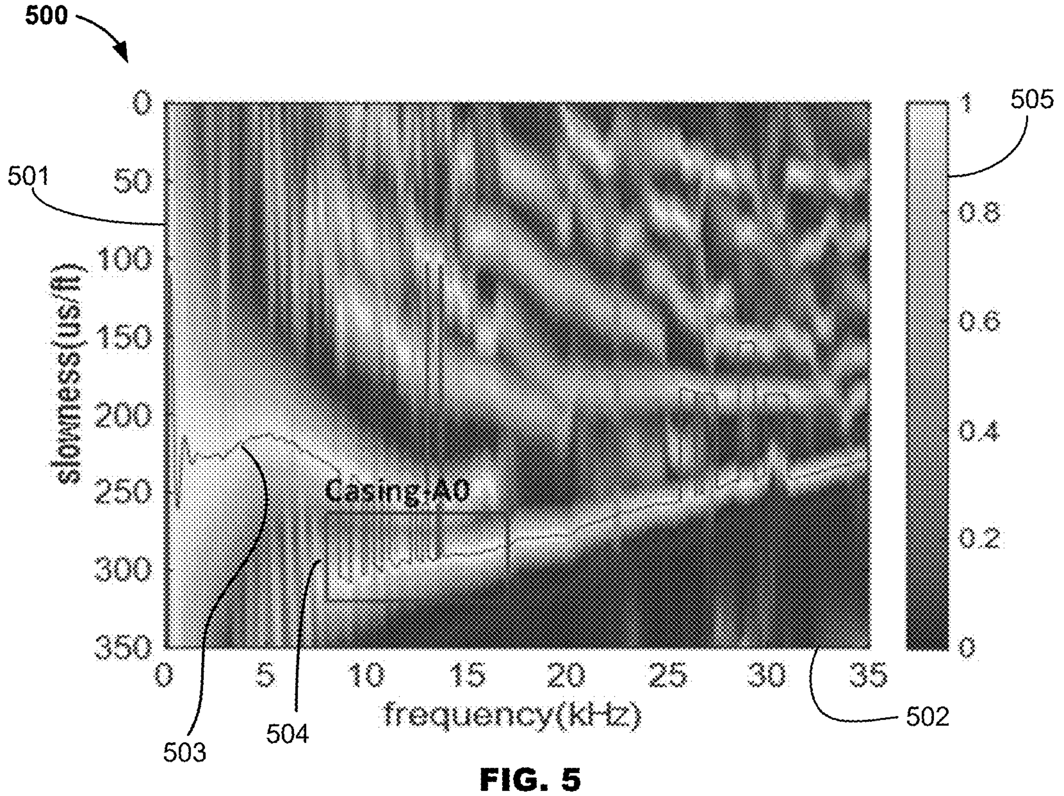
FIG. 5 shows a graph illustrating a dispersion analysis of the waveforms in FIG. 4, according to various embodiments.

FIG. 5 shows a graph 500 illustrating a dispersion analysis of the waveforms in FIG. 4 received at a fixed depth and fixed azimuth with a cased wellbore, according to various embodiments. Graph 500 includes a vertical axis 501 indicative of slowness in microseconds/foot (μs/ft), and a horizontal axis 502 indicative of frequency in kilohertz (kHz). Scale 505 represents a unitless grey-scale that is indicative of semblance values. Graphical line 503 represents extracted modal dispersions. The range of frequencies of the A0 waves within window 504 are selected as being usable for evaluation of the quality of the cement bonding to the casing in the area where the sonic waveforms were collected.

The peaks in graph 500 represent modal waves. Different methods may be used to create the semblance map, for example, the Prony method, the matrix-pencil method, the DPFS method. In various embodiments, the casing A0 wave has the highest slowness among all the modes at low frequencies. The semblance map allows for identification of the picking window 504 for the casing A0 waves. In other cases, the dispersion analysis may be applied to simulated data for window selection. Alternatively, the governing equation of the multilayer model with a tubing layer, a casing layer, and a cement layer may be directly solved to understand the dispersions of target A0 signals.

Figure 6:
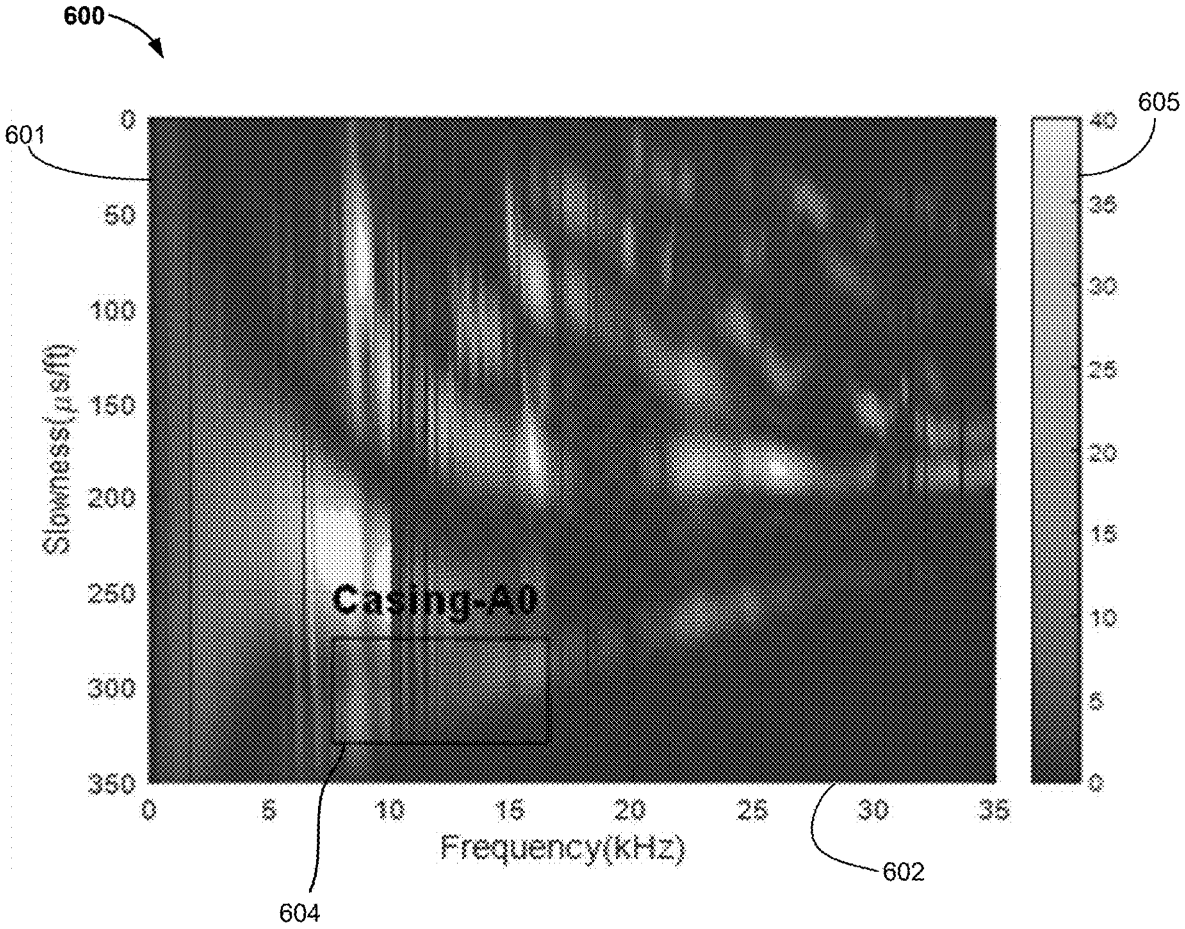
FIG. 6 shows a graph illustrating an example of amplitude map estimates produced using a beamforming method, according to various embodiments.

Based on the extracted dispersion of the target A0 waves, for each depth and azimuth, the raw waveform data are converted to a slowness-frequency amplitude map in the slowness-frequency domain, for example, by the beamforming method or the T-p transform. FIG. 6 shows a graph 600 illustrating an example of amplitude map estimates produced using a beamforming method, according to various embodiments. Graph 600 includes a vertical axis 601 indicative of slowness in microseconds/foot (μs/ft), and a horizontal axis 602 indicative of frequency in kilohertz (kHz). Scale 605 represents a unitless grey-scale indicative of modal amplitude. Window 604 represents a window of frequencies within the amplitude map of the A0 waves that are to be used for further processing for evaluating the cement bonding to the casing in the area where the sonic measurements were taken.

Calculating the summation, average, or root-square-mean values of the amplitude map in the window represented by window 604 determined by the semblance map yields the amplitude estimate of the A0 modes. The beamforming method is one of the methods that may be used to generate the amplitude map. In various embodiments, other ways may be used to create the amplitude map, including but not limited to the Fourier transform, the T-p transform, and the radon transform. After extracting the amplitude information of A0 waves for different azimuths and depths, a map of the A0 waves may be obtained that can be used to describe the bonding condition behind the casing.

Figure 7B:
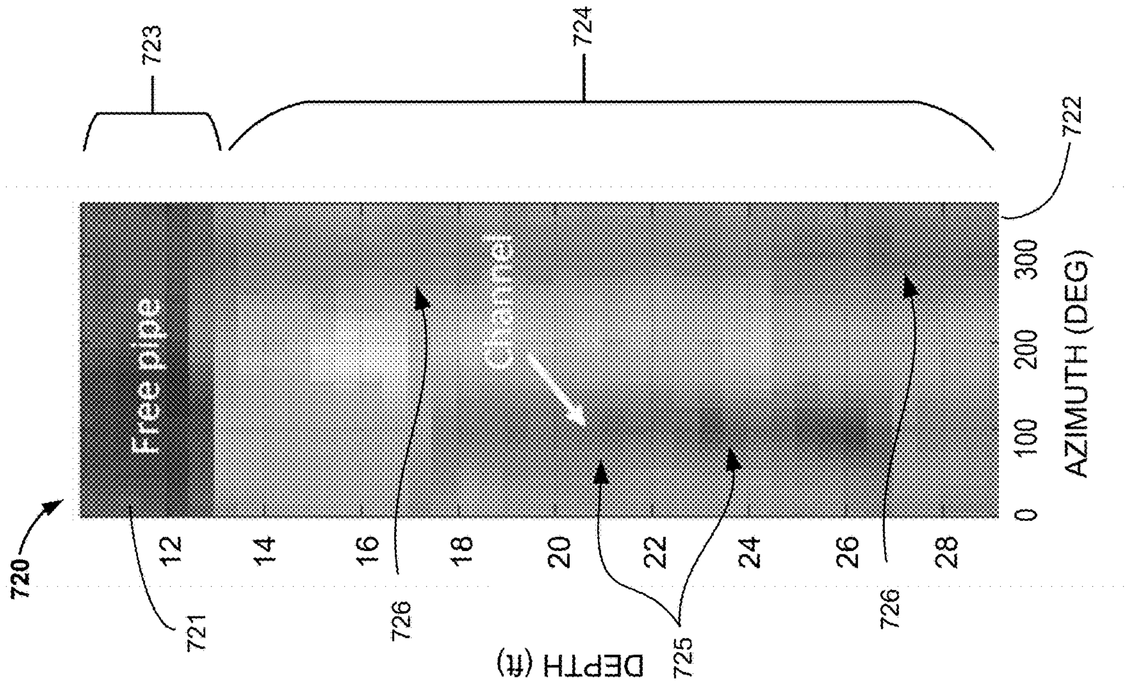
FIG. 7B is a graph illustrating an A0 amplitude map of the same cement bonding conditions of a wellbore as shown in FIG. 7A.
Figure 7A:
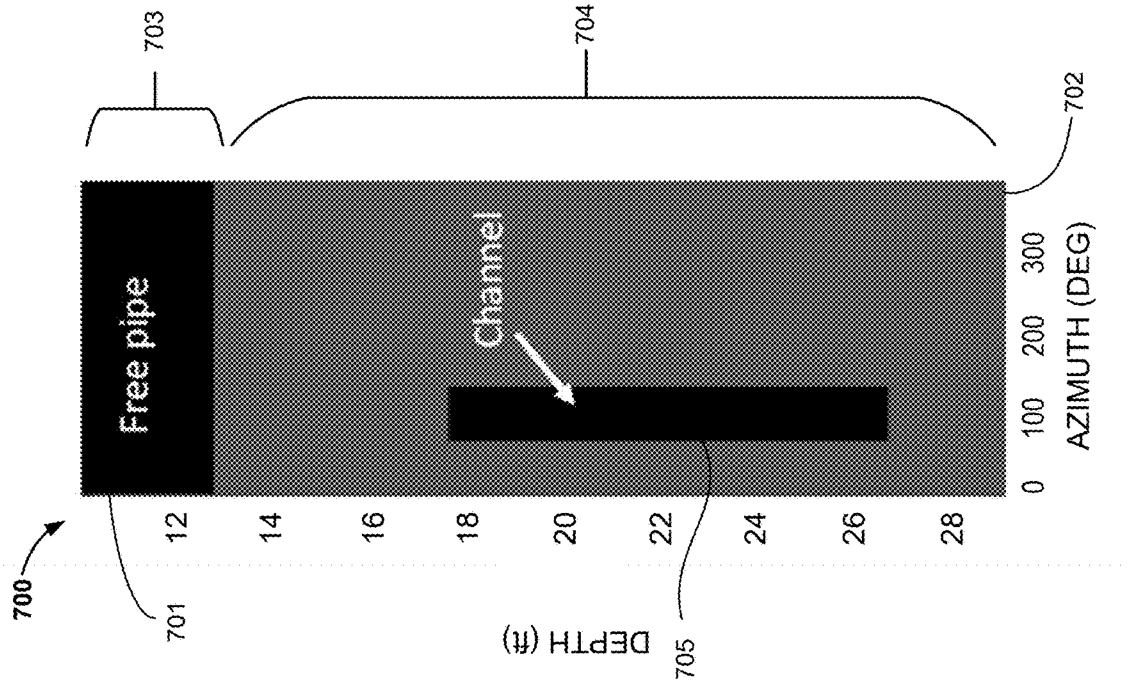
FIG. 7A is a graphical depictional of actual cement bond conditions in a wellbore.

For example, FIGS. 7A and 7B show a set of processing A0 amplitude from lab test data. FIG. 7A is a graphical depictional 700 of actual cement bond conditions in a wellbore. Graphical depiction 700 includes a vertical axis 701 indicative of depth of the wellbore in feet (ft), and a horizontal axis 702 indicative of azimuthal position around the wellbore in degrees (Deg). The portion of graphical depiction 700 to the left of bracket 703 represents a portion of the wellbore including free pipe that is not cemented, wherein the portion of graphical depiction 700 to the left of bracket 704 represents a portion of the wellbore where the casing is or is intended to be cemented to the inner surfaced of the wellbore.

FIG. 7B is a graph 720 illustrating a A0 amplitude map of the same cement bonding conditions of a wellbore as shown in FIG. 7A. Graph 720 as illustrated in FIG. 7B includes a vertical axis 721 indicative of depth of the wellbore in feet (ft) and corresponding to the same range of depths depicted in graphical depiction 700 (FIG. 7A), and a horizontal axis 722 indicative of azimuthal position around the wellbore in degrees (Deg), and corresponding to the azimuthal range as depicted in graphical depiction 700 (FIG. 7A). The portion of graph 720 to the left of bracket 723 represents a portion of the wellbore including free pipe that is not cemented, wherein the portion of graph 720 to the left of bracket 724 represents a portion of the wellbore where the casing is or is intended to be cemented to the inner surfaced of the wellbore.

FIG. 7A shows the ground truth of the bonding condition of the well, while FIG. 7B shows the estimated A0 amplitude map versus depth and azimuth with a sonic tool, such as sonic tool 120 (FIG. 1). As illustrated and described above with respect to FIG. 1, the tubing 110 is eccentric towards 90-degree, while the sonic tool 120 is centered in the tubing. From FIG. 7B, it is shown that the A0 amplitude shows a particular shading an areas of low amplitude A0 waves, indicative of channels and free pipe. For example, the shading represented the area 725, labeled as "Channel" in FIG. 7B, represents an area of the casing were cement is not well bonded to the casing, or is absent, represented as area 705 in FIG. 7A. Thus, this the A0 map may be used to calculate the bonding condition behind the casing.

Also illustrated in FIG. 7B is a variation in the levels of shading shown that is due to the tubing eccentricity. In graph 720 the A0 amplitude map in the zones without channels shows variations of the amplitude values, called the eccentricity effect. This eccentricity effect creates darker shaded band 726 at the azimuth against the eccentricity direction, and this darker shaded band does not correspond to any channels; thus, in various embodiments it is removed from the A0 map using an eccentricity calibration to remove the eccentricity effects. To do this, the data is first classified into different eccentricity ranges using the input eccentricity information. For a specific eccentricity range, for example, 40% to 50%, the A0 data with good bonding conditions is collected, and using the good-bond data, a set of calibration factors for different azimuths is generated. The calibration factors may be the median or averaged values of the selected data sets. For example, in FIG. 7B, the data between the depths of 13 and 17 feet are chosen as good bond data, and the median values for each azimuth are calculated as the calibration factors. To apply the calibration, the original map of graph 720 (FIG. 7B) is divided by the calibration factors, and used to generate the calibrated A0 map amplitude, as further illustrated and described below with respect to FIG. 8.

Figure 8:
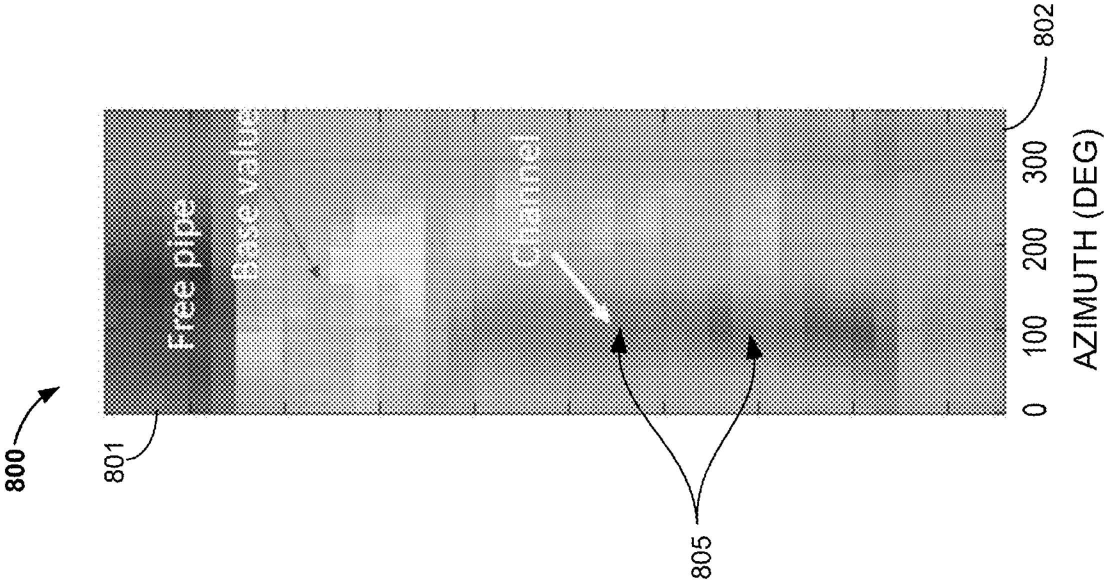
FIG. 8 shows a graph of the calibrated A0 map of FIG. 7B after eccentricity calibration, according to various embodiments.

FIG. 8 shows a graph 800 of the calibrated A0 map of FIG. 7B after eccentricity calibration, according to various embodiments. Graph 800 as illustrated in FIG. 8 includes a vertical axis 801 indicative of depth of the wellbore in feet (ft) and corresponding to the same range of depths depicted in graph 720 (FIG. 7B), and a horizontal axis 802 indicative of azimuthal position around the wellbore in degrees (Deg), and corresponding to the azimuthal range as depicted in graph 720 (FIG. 7B). As shown in graph 800, the darker band created by eccentricity in FIG. 7B is completely or almost completely removed, resulting in a unified A0 map response in the areas of the casing that are fully bonded with the cement behind the casing. The portion of the casing were the channel is present, representing poorly bonded or missing cement behind the case, is represented by areas 805, indicated as "Channel" in graph 800.

The final step is to map the A0 amplitude values to a bonding condition map. First, a base value is selected from the well-bond zone, indicated as "Base value" in graph 800, then the area whose values are close to the base values is identified as the good-bond zone, and the others are identified as channeled zones. The bonding condition is calculated based on the difference between the A0 amplitude and the base value.

Figure 9:
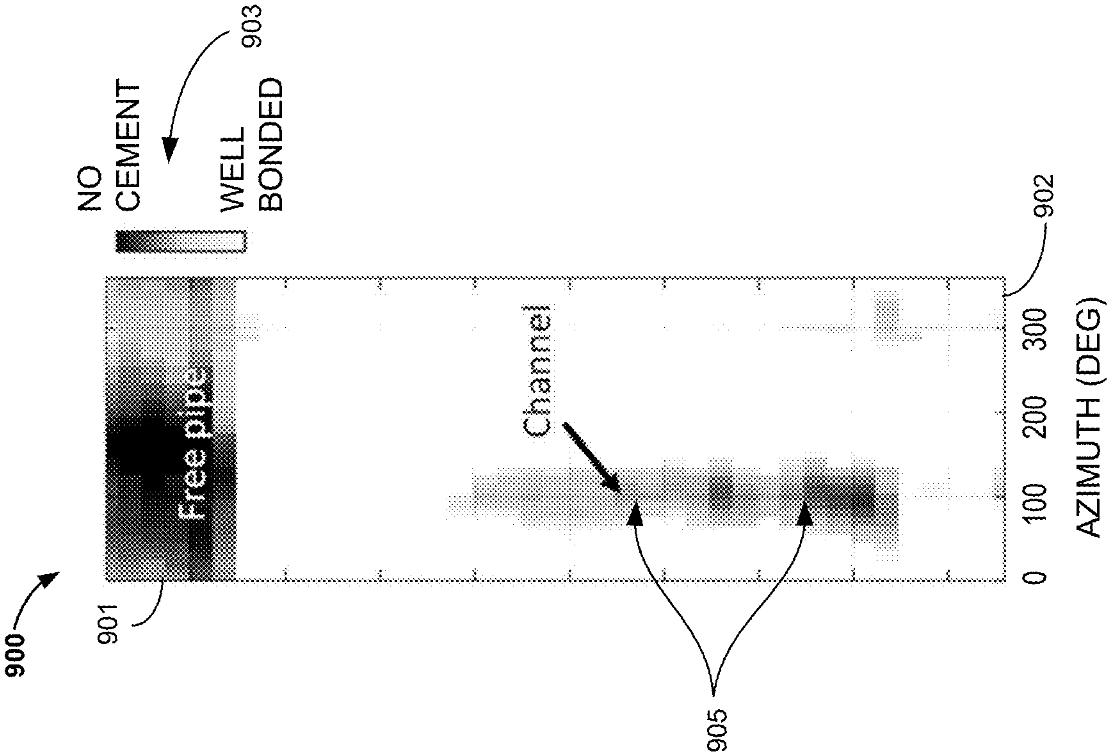
FIG. 9 shows a graph a bonding map generated using the calibrated A0 map of FIG. 9, according to various embodiments.

FIG. 9 shows a graph a bonding map generated using the calibrated A0 map of FIG. 9, according to various embodiments. Graph 900 as illustrated in FIG. 9 includes a vertical axis 901 indicative of depth of the wellbore in feet (ft) and corresponding to the same range of depths depicted in graph 800 (FIG. 8), and a horizontal axis 902 indicative of azimuthal position around the wellbore in degrees (Deg), and corresponding to the azimuthal range as depicted in graph 800 (FIG. 8).

As shown in graph 900 of FIG. 9, after calibration, the darker shaded band created by eccentricity is almost fully removed, resulting in a unified A0 map response in the full-bonded zones. The unitless scale 903 shown grey-scale coloration utilized in graph 900, wherein the lightest shades represent area where the cement is well bonded to the casing of a wellbore, and the darker areas represent areas where a channel exits in the cement outside of the casing. As shown in graph 900, the channel indicated by area 905 includes darker shaded areas indicative of the channel present in the cement behind the casing.

The disclosure as further described below also discloses workflows to introduce a time-spatial window in the processing to enable the time-spatial resolution. For example, before the step of 'create a slowness-frequency amplitude map with beamforming', a time-spatial window may be applied in the raw array waveforms to enhance the data of interest in the time-spatial domain. The time-spatial window can be estimated based on the starting Transmitter-Receiver (TR) offset and the travel time of target modes calculated from numerical simulations.

Figure 10:
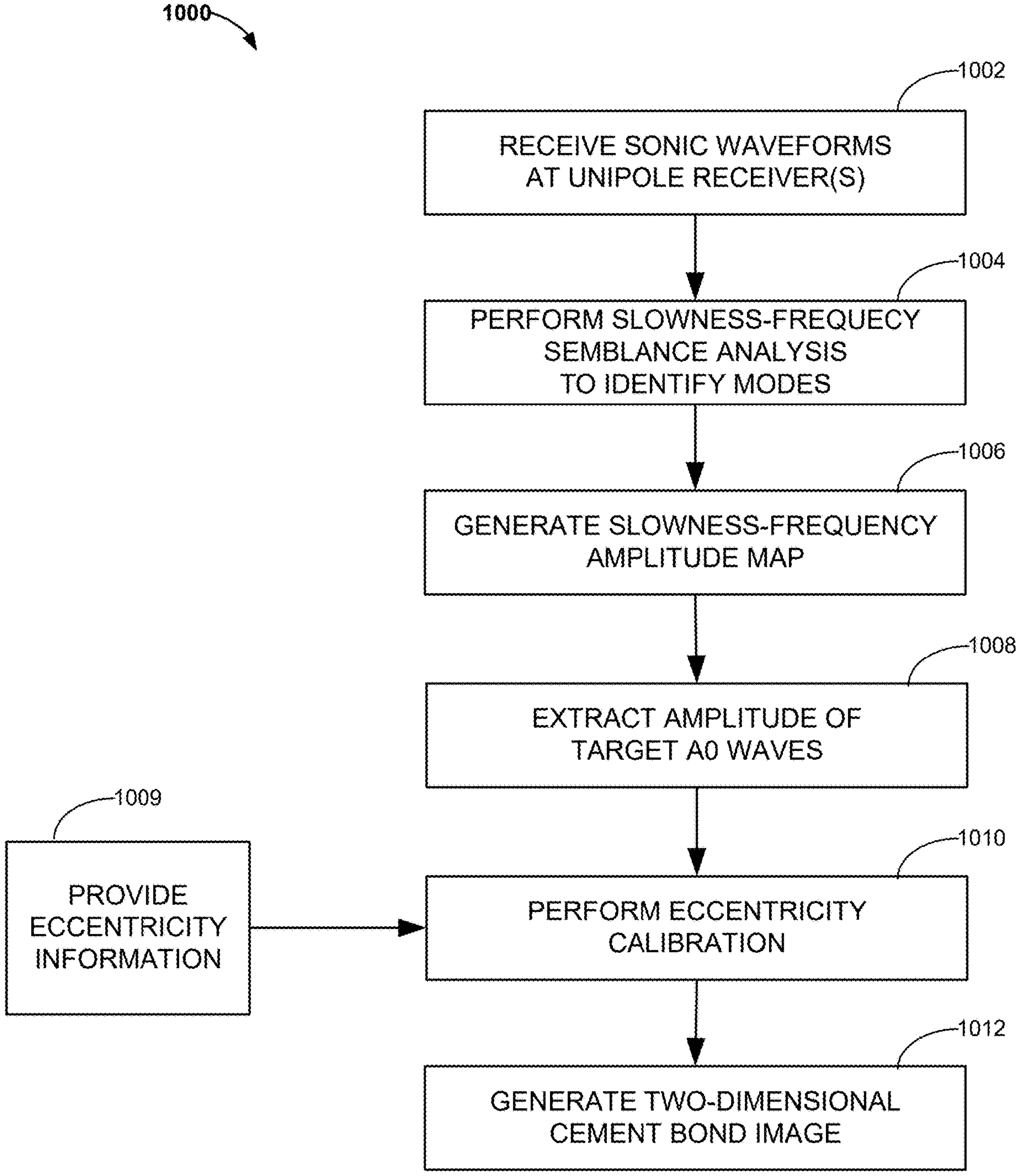
FIG. 10 is a flowchart illustrating a method for cement evaluation with low-frequency A0 waves, according to various embodiments.

FIG. 10 is a flowchart 1000 illustrating a method for cement evaluation with low-frequency A0 waves, according to various embodiments. The method depicted in flowchart 1000 may be performed by a system, such as system 100 and including a sonic tool 120, as illustrated and described above with respect to FIG. 1. The method may be applied to monopole transmitters and unipole receivers, including systems having just one receiver, or a plurality of receivers. The method can also be applied to wellbore systems wherein the sonic tool is deployed and operated in a wellbore having a casing, wherein the sonic tool may or may not be deployed and operated without a tubing positioned within the casing. Some operations included in the method depicted in flowchart 1000 may be performed by a computing device, such as computing system 1200, including one or more processors, as illustrated and described below with respect to FIG. 12.

Referring again to flowchart 1000 and FIG. 10, at block 1002 the method includes receiving sonic waves at one or more receivers positioned within a casing of a wellbore. In various embodiments, the one or more receivers are located on a sonic tool, which also includes a transmitter configured to generate sonic waves and transmit the sonic waves toward and into the casing. In various embodiments, the sonic waves generated by the transmitter are a pulsed sound wave having a frequency range of 500 to 40000 hertz. In various embodiments, the pulsed sound wave has a duration of 0.0001 seconds, and comprise a series of pulsed sound waves spaced apparat in time by 0.1 seconds, with a duty cycle of 0.1 percent.

After receiving the sonic waveforms at the one or more receivers, at block 1004 the method of flowchart 1000 includes performing a slowness-frequency semblance analysis, which is applied to a set of selected data to extract the dispersion of the target A0 waves. In various embodiments, the slowness-frequency semblance analysis comprises DPFS. In various embodiments, the target A0 waves are the A0 wave present over a predefined range of frequencies, such as but not limited to the range of frequencies depicted by window 504 in FIG. 5. After performing the slowness-frequency semblance analysis to extract the dispersion of the target A0 waves, the method of flowchart 1000 at block 1006 includes for each depth and azimuth, the raw waveform data are converted to generate a slowness-frequency amplitude map in the slowness-frequency domain. In various embodiments, the conversion is by a beamforming method. In various embodiments, the conversion is performed using T-p transform.

At block 1008, the method of flowchart 1000 includes extracting the amplitude of the target A0 wave from the slowness-frequency amplitude map using a slowness-frequency window determined by the slowness-frequency semblance analysis. This step of the method may include displaying the amplitude values in the depth-azimuth plane to yield a raw amplitude map.

At block 1010, embodiments of the method of flowchart 1000 include performing eccentricity calibration to remove the tubing eccentricity effect. Eccentricity calibration may be performed using tubing eccentricity information that are generated from the third interface echo (TIE), and provided (block 1009) in order to generate the eccentricity calibration. This step of the method would normally be performed when a tubing was present with the casing where the measurements using a sonic tool to transmit and receive the sonic waveforms received at block 1002 was present in the wellbore system.

At block 1012, the method of flowchart 1000 includes identifying the baseline of the well-bond zone response(s) and using that baseline to map the two-dimensional (depth-azimuthal) cement bond image from the eccentricity calibrated amplitude image. The two-dimensional cement bond image may be used to determine the quality of the cement bond to a casing of a wellbore system, and/or to determine the presence and location of any channels in the cement bonding the casing within the borehole of the wellbore system.

Figure 11:
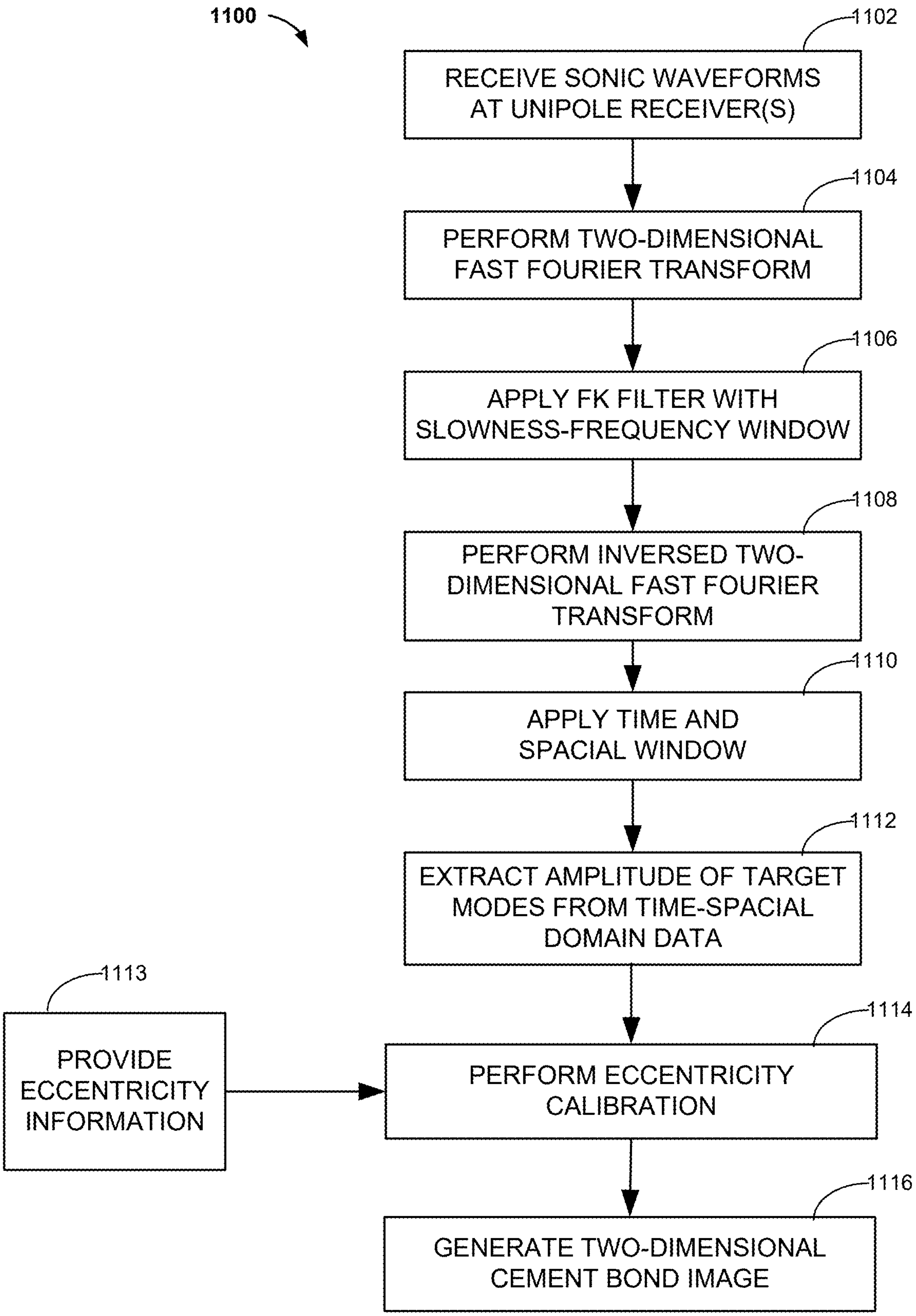
FIG. 11 is a flowchart of another method for cement evaluation with low-frequency A0 waves, according to various embodiments.

FIG. 11 is a flowchart 1100 illustrating a method for cement evaluation with low-frequency A0 waves, according to various embodiments. The method depicted in flowchart 1100 may be performed by a system, such as system 100 and including a sonic tool 120, as illustrated and described above with respect to FIG. 1. The method may be applied to monopole transmitters and unipole receivers, including systems having just one receiver, or a plurality of receivers. The method can also be applied to wellbore systems wherein the sonic tool is deployed and operated in a wellbore having a casing, wherein the sonic tool may or may not be deployed and operated without a tubing positioned within the casing. Some operations included in the method depicted in flowchart 1100 may be performed by a computing device, such as computing system 1200, including one or more processors, as illustrated and described below with respect to FIG. 12. Embodiments of the method of flowchart 1100 include performing the amplitude extraction from the A0 amplitude map in the time-spatial domain.

In FIG. 11 at block 1102 the method of flowchart 1100 includes receiving sonic waves at one or more receivers positioned within a casing of a wellbore. In various embodiments, the one or more receivers are located on a sonic tool, which also includes a transmitter configured to generate sonic waves and transmit the sonic waves toward and into the casing. In various embodiments, the sonic waves generated by the transmitter are a pulsed sound wave having a frequency range of 500 to 40000 hertz. In various embodiments, the pulsed sound wave has a duration of 0.0001 seconds, and comprise a series of pulsed sound waves spaced apparat in time by 0.1 seconds, with a duty cycle of 0.1 percent.

After receiving the sonic waveforms at the one or more receivers, at block 1104 the method of flowchart 1100 includes performing a two-dimension (2D) fast Fourier transform (FFT) to obtain the frequency-wavenumber (FK) spectra of the data.

At block 1106, the method of flowchart 1100 includes applying a frequency-wavenumber (FK) filter with a slowness frequency window of the target mode to the FK spectra.

At block 1108, the method of flowchart 1100 includes performing an inversed two-dimensional Fast Fourier transform to obtain the filtered time-spatial waveform data.

At block 1110, the method of flowchart 1100 includes applying a time-spatial window to enhance the data of interest in the time-spatial domain.

At block 1112, the method of flowchart 1100 includes extracting the amplitude of the target modes from the time-spatial domain data. In various embodiments, the extraction of the amplitude includes taking a root-square mean or area of the signal with a designated window.

At block 1114, embodiments of the method of flowchart 1100 include performing eccentricity calibration to remove the tubing eccentricity effect. Eccentricity calibration may be performed using tubing eccentricity information that are generated from the third interface echo (TIE), and provided (block 1113) in order to generate the eccentricity calibration. This step of the method would normally be performed when a tubing was present with the casing where the measurements using a sonic tool to transmit and receive the sonic waveforms received at block 1002 was present in the wellbore system.

At block 1116, the method of flowchart 1100 includes identifying the baseline of the well-bond zone response(s) and using that baseline to map the two-dimensional (depth-azimuthal) cement bond image from the eccentricity calibrated amplitude image. The two-dimensional cement bond image may be used to determine the quality of the cement bond to a casing of a wellbore system, and/or to determine the presence and location of any channels in the cement bonding the casing within the borehole of the wellbore system.

Figure 12:
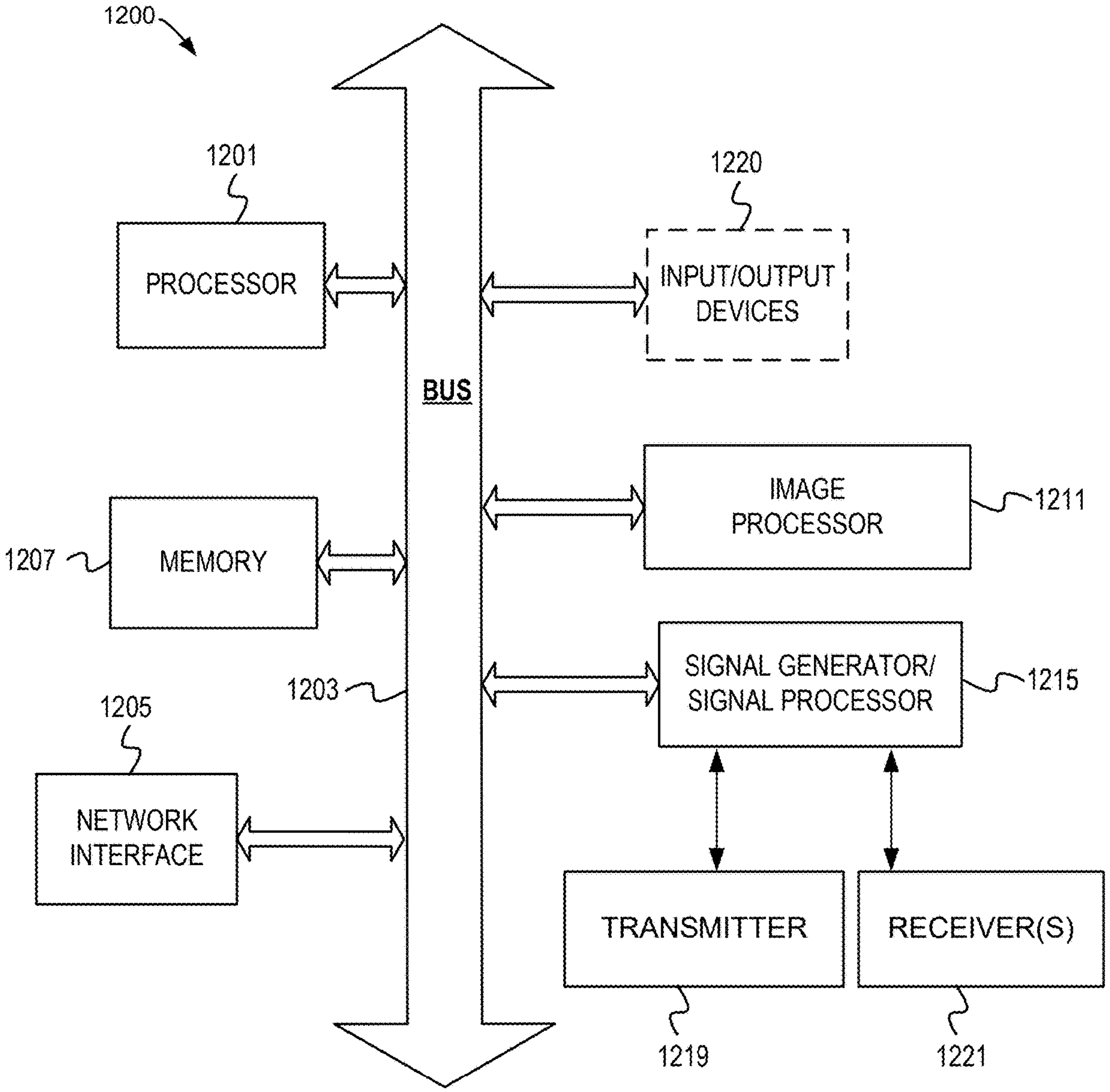
FIG. 12 illustrates a block diagram of an example computing system that may be employed to practice the concepts, methods, and techniques disclosed herein, and variations thereof.

FIG. 12 illustrates a block diagram of an example computing system 1200 that may be employed to practice the concepts, methods, and techniques disclosed herein, and variations thereof. The computing system 1200 includes a plurality of components of the system that are in electrical communication with each other, in some examples using a bus 1203. The computing system 1200 may include any suitable computer, controller, or data processing apparatus capable of being programmed to carry out the methods and apparatus as further described herein. In various examples, one or more components illustrated and described with respect to computing system 1200 may be included in sonic tool 120 and/or in positioning control system 130 as illustrated and described with respect to FIG. 1.

Referring back to FIG. 12, computing system 1200 may be a general-purpose computer, and include a processor 1201 (possibly including multiple processors, multiple cores, multiple nodes, and/or implementing multi-threading, etc.). The computer includes memory 1207. The memory 1207 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the possible realizations of non-transitory machine-readable media. The computer system also includes the bus 1203 (e.g., PCI, ISA, PCI-Express, HyperTransport® bus, InfiniBand® bus, NuBus, etc.) and a network interface 1205 (e.g., a Fiber Channel interface, an Ethernet interface, an internet small computer system interface, SONET interface, wireless interface, etc.). Network interface 1205 may be configured to provide communication between computer system 1200 and one or more other devices.

The computer may also include an image processor 1211. Image processor 1211 may be configured to produce graphical display data related to the cement evaluation data, which may then be displayed on a display device, such as display included in input/output devices 1220. Various embodiments of system 1200 include a signal generator/signal processor, hereinafter "controller" 1215. In various embodiments, controller 1215 is coupled to transmitter 1219, and is configured to generate sonic waveforms that are then provided to the transmitter for transmission into a casing of a wellbore system, such as casing 104 of system 100 (FIG. 1). Controller 1215 may also be coupled to one or more receivers 1221. Receivers 1221 may be configured to receive sonic waves dissipated through a casing of a wellbore, such as casing 104 of system 100 (FIG. 1), and also dissipated through a tubing when present in the casing, along with any fluid(s) present in the casing and/or the tubing when present. Controller 1215 may be configured to perform signal processing on measurement data received by receivers 1221. In various embodiments, controller 1215 includes circuitry and/or software functions, such as analog-to-digital (A/D) converters and buffers that allow controller 1215 to receive electrical signals directly from one or more of the receivers 1221 and to further process these electrical signal into a desired format for additional data processing.

In various embodiments, processor 1201 may be configured to generate control signals to control the different operations that may be performed for positioning of a sonic tool within a casing of a wellbore structure. For example, processor 1201 may generate control signals that may be used to control one or more actuators, such as actuator 132 (FIG. 1), to control the depth-wise positioning of a sonic tool with the wellbore structure. In various embodiments processor 1201 may generate control signal that may be used to control one or more actuators, such as actuator 132 (FIG. 1) and/or actuator 136 (FIG. 1), in order to control the azimuthal orientational positioning of a sonic tool with the wellbore structure.

Any one of the previously described functionalities may be partially (or entirely) implemented in hardware and/or on the processor 1201. For example, the functionality may be implemented with an application specific integrated circuit, in logic implemented in the processor 1201, in a co-processor on a peripheral device or card, etc. Further, realizations may include fewer or additional components not illustrated in FIG. 12 (e.g., video cards, audio cards, additional network interfaces, peripheral devices, etc.). For example, computing system 1200 may include some combination of input/output devices, such as computer keyboard, computer mouse, display monitors, and/or touch screens that allow a user, such as a technician or engineer, to interact with the computing system, including the uploading and downloading of data and programming to and from the system. As illustrated in FIG. 12, the processor 1201 and the network interface 1205 are coupled to the bus 1203. Although illustrated as also being coupled to the bus 1203, the memory 1207 may be coupled to the processor 1201 only, or both processor 1201 and bus 1203.

Processor 1201 may be configured to execute instruction that provide control over the positioning of a sonic tool with a wellbore structure, to control the generation and transmission of sonic wave directed toward the casing of the wellbore structure, to control receivers configured to detect sonic waves dissipated from the casing of the wellbore structure, and to process the detected sonic waves using and of the methods and techniques described in this disclosure.

With respect to computing system 1200, basic features here may easily be substituted for improved hardware or firmware arrangements as they are developed. In some examples, memory 1207 includes non-transient and/or non-volatile memory devices, and can be a hard disk or other types of computer readable media which can store data that are accessible by a computer, such as magnetic cassettes, flash memory cards, solid state memory devices, digital versatile disks (DVDs), cartridges, RAM, ROM, a cable containing a bit stream, and hybrids thereof.

It will be understood that one or more blocks of the flowchart illustrations and/or block diagrams, and combinations of blocks in the flowchart illustrations and/or block diagrams, can be implemented by program code. The program code may be provided to a processor of a general-purpose computer, special purpose computer, or other programmable machine or apparatus. As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine. While depicted as a computing system 1200 or as a general purpose computer, some embodiments can be any type of device or apparatus to perform operations described herein.

While the aspects of the disclosure are described with reference to various implementations and exploitations, it will be understood that these aspects are illustrative and that the scope of the claims is not limited to them. In general, techniques for automatically pressure testing frac iron described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

Example Embodiments Include the Following

Embodiment 1. A method comprising: receiving, at a sonic receiver, a set of waveforms induced in a casing of a borehole, wherein one or more portions of the casing include a cement layer bonding the casing to an inner surface of the borehole; perform a slowness-frequency semblance analysis on the waveforms to extract a dispersion of a target set of A0 waves; generating a slowness-frequency amplitude map in a slowness-frequency domain; extracting an amplitude for the target set of A0 wave from the slowness-frequency amplitude map using a slowness-frequency window determined by the slowness-frequency semblance analysis; and generating a two-dimensional cement bonding image based on the extracted amplitude of the target A0 waves.

Embodiment 2. The method of embodiment 1, further comprising: detecting a presence of a channel in the cement layer based on the two-dimensional cement bonding image.

Embodiment 3. The method of embodiments 1 or 2, wherein the slowness-frequency window includes frequencies in a range of 500 to 40000 Hz, inclusive.

Embodiment 4. The method of any one of embodiments 1-3, wherein generating the slowness-frequency amplitude map includes using a beamforming method.

Embodiment 5. The method of any one of embodiments 1-3, wherein generating the slowness-frequency amplitude map includes using one of the Prony method, the matrix-pencil method, or the Differential-Phase Frequency-semblance method.

Embodiment 6. The method of any one of embodiments 1-5, further including: receiving data generated by a third interface echo; generate a tubing eccentricity information from the data generated by the third interface echo; generate an eccentricity calibration based at least in part on the tubing eccentricity information; and calibrate the amplitude of the target A0 waves by removing a tubing eccentricity effect based on the eccentricity calibration.

Embodiment 7. The method of any one of embodiments 1-6, wherein receiving the set of waveforms induced in the casing of the borehole includes receiving the set of waveform from the casing through a wall of a production tubing positioned with an annulus encircled by the casing.

Embodiment 8. The method of any one of embodiments 1-7, further comprising: transmitting, using a sonic transmitter, a set of transmitted sonic waves directed toward and induced in the casing in order to generate the set of waveforms dispersed by the casing of the borehole.

Embodiment 9. The method of any one of embodiments 1-8, wherein generating a two-dimensional cement bonding image based on the extracted amplitude of the target A0 waves comprises: selecting a base value identified from a good-bond zone within the two-dimensional cement bonding image; and calculating a boding condition based on a difference between an A0 amplitude value and the base value.

Embodiment 10. A system comprising: a sonic tool configured to be lowered into a casing within a borehole of a wellbore extending into a subterranean formation, the sonic tool including a sonic transmitter and one or more sonic receivers, wherein the sonic transmitter is configured to generate and transmit into the casing a sonic signal comprising A0 waveforms, and wherein the one or more sonic receivers are configured to receive waveforms induced in the casing; and a processor configured to: input the received waveforms, perform slowness-frequency semblance analysis on the waveforms to extract a dispersion of a target set of A0 waves, generate a slowness-frequency amplitude map in a slowness-frequency domain, extract an amplitude for the target A0 wave from-using a slowness-frequency window determined by the slowness-frequency semblance analysis, and generate a two-dimensional cement bonding image based on the extracted amplitude of the target A0 waves.

Embodiment 11. The system of embodiment 10, wherein the processor is further configured to detect a presence of a channel in a cement layer positioned around the casing based on the two-dimensional cement bonding image.

Embodiment 12. The system of embodiments 10 or 11, wherein the slowness-frequency window includes frequencies in a range of 500 to 40000 Hz, inclusive.

Embodiment 13. The system of any one of embodiments 10-12, wherein the processor is further configured to: receive data generated by a third interface echo; generate a tubing eccentricity information from the data generated by the third interface echo; generate an eccentricity calibration based at least in part on the tubing eccentricity information; and calibrate the amplitude of the target A0 waves by removing a tubing eccentricity effect based on the eccentricity calibration.

Embodiment 14. The system of any one of embodiments 10-13, wherein the sonic tool is configured to be positioned within a tubing positioned present within a annulus encircled by the casing within the wellbore, and wherein the one or more sonic receivers are configured to receive waveforms from the casing through a wall of the tubing.

Embodiment 15. The system of any one of embodiments 10-14, wherein receiving the set of waveforms induced in the casing of the borehole includes receiving the set of waveform from the casing through a wall of a production tubing positioned with an annulus encircled by the casing.

Embodiment 16. The system of any one of embodiments 10-15, wherein the sonic transmitter is a unipole transmitter and the one or more sonic receivers are unipole receivers, wherein the sonic transmitter and the one or more sonic receivers are located on a same side of the sonic tool.

Embodiment 17. The system of any one of embodiments 10-16, wherein the sonic transmitter and the one or more sonic receivers are mounted on a rotary head configured to rotate and to transmit and receive one or more sonic signals at different azimuthal orientations within the borehole.

Embodiment 18. A non-transitory machine-readable storage medium having program code stored thereon and executable by a processor to cause the processor to: input a set of waveforms representing sonic waves induced in a casing of a borehole and detected by one or more receivers of a sonic tool, wherein one or more portions of the casing include a cement layer bonding the casing to an inner surface of the borehole; perform a slowness-frequency semblance analysis on the set of waveforms to extract a dispersion of a target set of A0 waves; generate a slowness-frequency amplitude map in a slowness-frequency domain; extract an amplitude for the target set of A0 wave from the slowness-frequency amplitude map using a slowness-frequency window determined by the slowness-frequency semblance analysis; and generate a two-dimensional cement bonding image based on the extracted amplitude of the target A0 waves.

Embodiment 19. The non-transitory machine-readable storage medium of embodiment 18, wherein the program code further comprises program code executable by the processor to cause the processor to: receive data generated by a third interface echo; generate a tubing eccentricity information from the data generated by the third interface echo; generate an eccentricity calibration based at least in part on the tubing eccentricity information; and calibrate the amplitude of the target A0 waves by removing a tubing eccentricity effect based on the eccentricity calibration.

Embodiment 20. The non-transitory machine-readable storage medium of embodiments 18 or 19, wherein the slowness-frequency window includes frequencies in a range of 500 to 40000 Hz, inclusive.

What is claimed is:

1. A method comprising:

receiving, at a plurality of unipole sonic receivers in a receiver array with rotation capability, a set of waveforms propagated through a casing of a borehole by at least one rotating unipole transmitter positioned within the borehole, wherein one or more portions of the casing include a cement layer bonding the casing to an inner surface of the borehole, and wherein rotation of the unipole transmitter and the plurality of unipole receivers enables acquisition of the set of waveforms at multiple azimuthal orientations and at different spatial receiver positions along the receiver array;

performing a slowness-frequency semblance analysis on the set of waveforms to extract a dispersion of a target set of low-frequency pseudo-Lamb A0 waves;

extracting amplitudes for the target set of low-frequency pseudo-Lamb A0 waves from a slowness-frequency amplitude map derived from the slowness-frequency semblance analysis; and generating, by an image processor, a two-dimensional cement bonding image representing bonding conditions behind the casing based on eccentricity-calibrated amplitude values derived from the extracted amplitudes of the target set of low-frequency pseudo-Lamb A0 waves and a baseline amplitude defined by a good-bond zone within the two-dimensional cement bonding image.

2. The method of claim 1, further comprising:
detecting a presence of a channel in the cement layer based on the two-dimensional cement bonding image.

3. The method of claim 1, further comprising applying a time-spatial window to the target set of low-frequency pseudo-Lamb A0 waves, wherein the target set of low-frequency pseudo-Lamb A0 waves comprise one or more frequencies within a range of 500 to 40000 Hz, inclusive.

4. The method of claim 1, further comprising generating the slowness-frequency amplitude map using one of a beamforming method, a Prony method, a matrix-pencil method, or a Differential-Phase Frequency-semblance method.

5. The method of claim 1, wherein control of a rotational position includes controlling both a depth position within the casing and an azimuthal orientational position of the unipole sonic receivers and the rotating unipole transmitter.

6. The method of claim 1, further including:
receiving data generated by a third interface echo;
generating tubing eccentricity information from the data generated by the third interface echo;
generating an eccentricity calibration based at least in part on the tubing eccentricity information; and
calibrating the amplitude of the target set of low-frequency pseudo-Lamb A0 waves by removing a tubing eccentricity effect based on the eccentricity calibration to determine the eccentricity-calibrated amplitude values.

7. The method of claim 1, wherein receiving the set of waveforms propagated through the casing of the borehole includes receiving the set of waveforms from the casing through a wall of a production tubing positioned with an annulus encircled by the casing.

8. The method of claim 1, further comprising:
transmitting, using a sonic transmitter, a set of transmitted sonic waves directed toward and induced in the casing in order to generate the set of waveforms dispersed by the casing of the borehole.

9. The method of claim 1, wherein generating the two-dimensional cement bonding image comprises:
selecting the baseline amplitude identified from the good-bond zone within the two-dimensional cement bonding image; and
calculating a bonding condition based on a difference between an A0 amplitude value of at least one of the low-frequency pseudo-Lamb A0 waves and the baseline amplitude.

10. A system comprising:
a sonic tool configured to be lowered into a casing within a borehole of a wellbore extending into a subterranean formation, the sonic tool including a rotating unipole sonic transmitter, one or more unipole sonic receivers in a receiver array with rotation capability, and one or more actuators, the actuators configured to provide rotational motion and control of a rotational position of the sonic tool,
wherein the rotating sonic transmitter is configured to generate and transmit into the casing a sonic signal comprising A0 waveforms, and
wherein the one or more unipole sonic receivers are configured to receive the A0 waveforms as a set of waveforms propagated through the casing; and
a processor configured to:
input the received set of waveforms,
perform slowness-frequency semblance analysis on the set of waveforms to extract a dispersion of a target set of low-frequency pseudo-Lamb A0 waves, and
extract amplitudes for the target set of low-frequency pseudo-Lamb A0 waves from a slowness-frequency amplitude map derived from the slowness-frequency semblance analysis, and
an image processor configured to generate a two-dimensional cement bonding image representing bonding conditions behind the casing based on eccentricity-calibrated amplitude values derived from the extracted amplitudes of the target set of low-frequency pseudo-Lamb A0 waves and a baseline amplitude defined by a good-bond zone within the two-dimensional cement bonding image.

11. The system of claim 10, wherein the processor is further configured to detect a presence of a channel in a cement layer positioned around the casing based on the two-dimensional cement bonding image.

12. The system of claim 10, further comprising applying a time-spatial window to the target set of low-frequency pseudo-Lamb A0 waves, wherein the target set of low-frequency pseudo-Lamb A0 waves comprise one or more frequencies within a range of 500 to 40000 Hz, inclusive.

13. The system of claim 10, wherein the processor is further configured to:
receive data generated by a third interface echo;
generate tubing eccentricity information from the data generated by the third interface echo;
generate an eccentricity calibration based at least in part on the tubing eccentricity information; and
calibrate the amplitude of the target set of low-frequency pseudo-Lamb A0 waves by removing a tubing eccentricity effect based on the eccentricity calibration to determine the eccentricity-calibrated amplitude values.

14. The system of claim 10,
wherein the sonic tool is configured to be positioned within a tubing present within an annulus encircled by the casing within the wellbore, and
wherein the one or more unipole sonic receivers are configured to receive waveforms from the casing through a wall of the tubing.

15. The system of claim 10, wherein receiving the set of waveforms propagated through the casing of the borehole includes receiving the set of waveforms from the casing through a wall of a production tubing positioned with an annulus encircled by the casing.

16. The system of claim 10, wherein the unipole sonic transmitter and the one or more unipole sonic receivers are located on a same side of the sonic tool.

17. The system of claim 10, wherein the unipole sonic transmitter and the one or more unipole sonic receivers are mounted on a rotary head configured to rotate and to transmit and receive one or more sonic signals at different azimuthal orientations within the borehole.

18. A non-transitory machine-readable storage medium having program code stored thereon and executable by a processor to cause the processor to:
input a set of waveforms representing sonic waves propagated through a casing of a borehole by one or more rotating unipole sonic transmitters and detected by one or more unipole sonic receivers with rotation capability provided by a sonic tool, wherein one or more portions of the casing include a cement layer bonding the casing to an inner surface of the borehole;

perform a slowness-frequency semblance analysis on the set of waveforms to extract a dispersion of a target set of low-frequency pseudo-Lamb A0 waves;

extract amplitudes for the target set of low-frequency pseudo-Lamb A0 waves from a slowness-frequency amplitude map derived from the slowness-frequency semblance analysis; and generate, using an image processor, a two-dimensional cement bonding image representing bonding conditions behind the casing based on eccentricity-calibrated amplitude values derived from the extracted amplitudes of the target set of low-frequency pseudo-Lamb A0 waves and a baseline amplitude defined by a good-bond zone within the two-dimensional cement bonding image.

19. The non-transitory machine-readable storage medium of claim 18, wherein the program code further comprises program code executable by the processor to cause the processor to:

receive data generated by a third interface echo;

generate a tubing eccentricity information from the data generated by the third interface echo;

generate an eccentricity calibration based at least in part on the tubing eccentricity information; and calibrate the amplitude of the target set of low-frequency pseudo-Lamb A0 waves by removing a tubing eccentricity effect based on the eccentricity calibration to determine the eccentricity-calibrated amplitude values.

20. The non-transitory machine-readable storage medium of claim 18, wherein the program code further comprises program code executable by the processor to cause the processor to:

apply a time-spatial window to the target set of low-frequency pseudo-Lamb A0 waves, wherein the target set of low-frequency pseudo-Lamb A0 waves comprise one or more frequencies within a range of 500 to 40000 Hz, inclusive.

* * * * *